United States Patent [19]

Scholl et al.

[11] 4,236,016
[45] Nov. 25, 1980

[54] PROCESS FOR THE PREPARATION OF URETHANES

[75] Inventors: Hans-Joachim Scholl, Cologne; Armin Zenner, Dormagen, both of Fed. Rep. of Germany

[73] Assignee: Bayer Aktiengesellschaft, Leverkusen, Fed. Rep. of Germany

[21] Appl. No.: 13,637

[22] Filed: Feb. 21, 1979

[30] Foreign Application Priority Data

Mar. 2, 1978 [DE] Fed. Rep. of Germany ....... 2808980

[51] Int. Cl.$^3$ .......................................... C07C 125/065
[52] U.S. Cl. ...................................... 560/24; 560/25; 560/27; 560/28
[58] Field of Search ................... 560/25, 24, 27, 28

[56] References Cited

U.S. PATENT DOCUMENTS

| 3,895,054 | 7/1975 | Zajacek et al. | 560/25 |
|---|---|---|---|
| 3,956,360 | 5/1976 | Zajacek et al. | 560/25 |
| 3,993,685 | 11/1976 | Zajacek et al. | 560/25 |
| 4,080,365 | 3/1978 | Hirai et al. | 560/25 |
| 4,130,633 | 12/1978 | Shawl et al. | 560/25 |
| 4,170,708 | 10/1979 | Hirai et al. | 560/25 |

FOREIGN PATENT DOCUMENTS 1472243 5/1977 United Kingdom .
1485108 9/1977 United Kingdom .

Primary Examiner—G. T. Breitenstein
Attorney, Agent, or Firm—Gene Harsh; Joseph C. Gil

[57] ABSTRACT

The instant invention relates to an improved process for the preparation of urethanes by the reaction of aromatic nitro compounds with alcohols and carbon monoxide in the presence of catalyst systems which contain selenium.

17 Claims, No Drawings

PROCESS FOR THE PREPARATION OF URETHANES

BACKGROUND OF THE INVENTION

Urethanes have in the past been prepared by the reaction of an aromatic isocyanate with an alcohol, the isocyanate generally having been obtained by the reaction of phosgene with the appropriate primary amine which in turn had generally been obtained by reduction of the corresponding nitro compound. This conventional process has various disadvantages. For example, the toxicity and corrosive nature of phosgene and the formation of hydrogen chloride as by-product have been particularly troublesome. It is also known that certain aromatic amines have harmful biological properties and some of them also tend to be oxidized by air in storage.

There have been many attempts to avoid the use of the highly toxic phosgene and to obtain urethanes directly from the corresponding nitro compounds and the corresponding alcohols and carbon monoxide. The processes according to U.S. Pat. No. 3,993,685 and German Offenlegungsschrift No. 2,603,574 used catalyst systems based on metals of the platinum group. Since considerable losses of the precious catalysts were unavoidable in these processes, they have not so far become established for production on an industrial scale.

In the process described in German Offenlegungsschrift No. 2,343,826, a combination of selenium or sulphur or compounds of these elements with very large quantities of a base was proposed as catalytically active system. The bases used included, for example, triethylamine and pyridine. In order to be able to start the reaction satisfactorily in the presence of these tertiary amines, it was necessary to use them in rather large quantities compared with the nitro compound used as starting material. In fact, when dinitrotoluene is used as the nitro compound, the quantity of tertiary amine used was equal to or greater than that of dinitrotoluene. The use of such large quantities of tertiary amine involves numerous problems of an ecomonic nature and, particularly with regard to the recovery process. Furthermore, this method leads to the formation of by-products such as amino compounds and ureas if measurable quantities of water are present, e.g. as hydrates or in the free form. The process according to German Offenlegungsschrift No. 2,343,826 was therefore unsuitable for application on a large commercial scale.

The reduction in yield of the desired urethanes due to the aforesaid formation of by-products is described as being avoided in the process according to German Offenlegungsschrift No. 2,614,101 by using a catalyst system which is composed of elementary selenium or a selenium compound and a promoter consisting e.g. of a bicyclic amidine and a carboxylic acid. Although the process according to German Offenlegungsschrift No. 2,614,101 resulted in higher yields of urethanes than the process according to German Offenlegungsschrift No. 2,343,826, it also led to disturbing quantities of by-products, particularly products of hydrolysis and of secondary reactions of the urethane formed.

The process according to German Offenlegungsschrift No. 2,623,694 is regarded as a further development of the process described in German Offenlegungsschrift No. 2,614,101 in that the formation of by-products from urethanes by the addition of aromatic amino compounds or aromatic urea compounds which correspond to these by-products was suppressed. Although this measure provided an improvement to the process of German Offenlegungsschrift No. 2,614,101, the process of Offenlegungsschrift No. 2,623,694 still had serious disadvantages. In particular, it required the use of exceptionally large quantities of selenium or selenium compounds, so that considerable losses of this catalyst necessarily occurred. Furthermore, selenium and the selenium compounds used as catalysts are toxicologically harmful substances apart from imparting an unpleasant odor to the urethane produced.

It was therefore an object of the present invention to provide an improved process for the production of urethanes from aromatic nitro compounds, alcohols and carbon monoxide in which the quantity of selenium or selenium compound could be very substantially reduced and urethane could be formed substantially quantitatively in spite of the reduction in the quantity of catalyst.

DESCRIPTION OF THE INVENTION

This problem was surprisingly solved by the process according to the instant invention. The quantity of selenium or selenium compound to be used according to the instant invention can be reduced so drastically that the problems of purification, toxicity and separation described above have been substantially eliminated.

The present invention therefore relates to a process for the preparation of urethanes by the reaction of aromatic nitro compounds with aliphatic, cycloaliphatic or araliphatic alcohols and carbon monoxide in the presence of catalyst systems containing selenium and/or selenium compounds and aromatic amino compounds and/or aromatic urea compound, characterized in that the catalyst systems used contain tertiary organic amines and/or alkali metal salts of weak acids. In addition oxidizing agents selected from the group consisting of oxygen, oxidizing organic compounds containing chemically bound oxygen and oxidizing inorganic compounds of metals of sub-Groups 1, 2 and 5–8 of the Periodic System of Elements containing chemically bound oxygen are included.

The following are starting compounds for the process according to the invention:

1. Aromatic nitro compounds, including nitrobenzene, 1,3-dinitrobenzene, o-nitrotoluene, m-nitrotoluene, p-nitrotoluene, 2,4-dinitrotoluene, 2,6-dinitrotoluene, nitronaphthalenes, nitroanthracenes, nitrobiphenylenes and the like. Nitro compounds suitable for the process according to the invention generally have a molecular weight of from 123 to 400 and have from 1 to 3 aromatic nuclei and from 1 to 3 nitro groups attached to aromatic nuclei. The nitro compounds optionally also contain other substituents which are inert under the reaction conditions of the process. Among the preferred nitro compounds for the process according to the invention are nitrobenzene and the above mentioned dinitrotoluenes. Any mixtures of the aforesaid nitro compounds may, of course, also be used.

2. Aliphatic, cycloaliphatic or araliphatic alcohols including any organic compounds with molecular weights of from 32 to 300 which have at least one aliphatically, cycloaliphatically or araliphatically bound hydroxyl group and which are otherwise inert under the reaction conditions. Examples of suitable alcohols include primary, secondary and tertiary alcohols such as methanol, ethanol, n-propanol, isopropanol, the various isomeric butanols, cyclohexylalcohol, benzyl alcohol, hexyl alcohol, lauryl alcohol, cetyl alcohol and the like. Monohydric alcohols are preferably used for the process of the invention, with ethanol being particularly preferred.

3. Gaseous carbon monoxide

Catalyst systems used in the process according to the invention contain (a) selenium or a selenium compound, (b) an oxidizing agent, (c) a tertiary organic amine and/or an alkali metal salt of a weak acid and (d) an aromatic amino compound and/or an aromatic urea compound.

The catalyst component (a) may be either elementary selenium in any form (preferably metallic selenium) or an inorganic selenium compound such as selenium dioxide or carbonyl selenide (COSe). It would theoretically be possible to use organic selenium compounds such as dimethylselenide, diphenylselenide or the like. Elementary selenium is particularly preferred.

The oxidizing agents (b) are either elementary oxygen or a gas containing oxygen, e.g. air, and/or organic compounds which contain chemically bound oxygen and have an oxidizing action, e.g. quinones, preferably 1,4-benzoquinone, and/or inorganic compounds of metals which contain chemically bound oxygen and have an oxidizing action. The last mentioned compounds include, in particular, the corresponding oxides. It is preferred to use the corresponding metal compounds of elements of sub-Group 2 and sub-Groups 5 to 8 of the Periodic System but it is particularly preferred to use the corresponding compounds of elements of sub-Groups 5 and 6 and the corresponding compounds of manganese, iron, cobalt and nickel. Examples of suitable oxidizing agents include zinc oxide, iron-II oxide, iron-III oxide, mixed oxides of the last mentioned iron oxides, vanadium-V oxide, manganese-IV-oxide, molybdenum-VI oxide, nickel-II oxide, cobalt-II oxide, mixed oxides of trivalent to hexavalent chromium, and any mixtures of the oxides exemplified above. Iron-III oxide is one of the particularly preferred oxidizing agents. Mixed oxides containing iron, vanadium and/or molybdenum are particularly preferred.

The catalyst components (c) include organic bases containing tertiary amino groups, such as tertiary aliphatic amines having a total of from 3 to 20 carbon atoms, such as trimethylamine, triethylamine, N,N-dimethyloctadecylamine or trihexylamine, heterocyclic tertiary amines such as pyridine, or amines containing two tertiary amino groups, e.g. diazabicyclo[2,2,2]-octane (triethylene diamine) or bicyclic amidines corresponding to the following formula

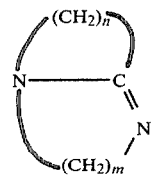

in which
n represents an integer of from 3 to 5 and
m represents an integer of from 2 to 4.

In addition to or instead of the above mentioned tertiary amines, alkali metal salts of weak acids which are basic in the reaction may also be used as catalyst component (c). Particularly preferred are alkali metal carboxylates such as sodium acetate, potassium acetate, sodium benzoate or alkali metal salts of weak inorganic acids, e.g. sodium borate or sodium carbonate. Among the preferred catalyst components (c) are included 1,5-diazabicyclo[4,3,0]-non-5-ene; 1,8-diazabicyclo[5,4,0]-undecene-7 and sodium and potassium acetate. Triethylenediamine is also a preferred compound, particularly in combination with salts of the formula MeX in which
Me represents an alkali metal cation and
X represents an iodide, cyanate or thiocyanate anion.

When combinations of organic base and salts are used, the last mentioned salts are generally used in quantities of from 1 to 40 mol %, preferably 4 to 20 mol %, based on the quantity of nitro compound used.

Catalyst component (d) may be any organic compound which contains aromatically bound primary amino groups and/or aromatically bound urea groups and may in particular contain nitro groups and urethane groups in addition to the aforesaid groups. Component (d) of the catalyst systems used according to the invention generally consist of compounds or mixtures of compounds corresponding to the following formulae $$A \begin{matrix} \nearrow (NH_2)_x \\ -(NHCO_2R)_y \\ \searrow (NO_2)_z \end{matrix}$$

and/or

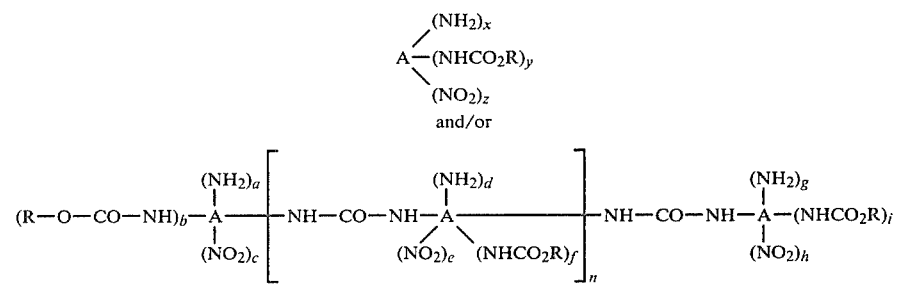

wherein
$x = 1$ or 2,
$y = 0$ or 1,
$z = 0$ or 1, and the sum of $x+y+z$ is preferably 1 or 2; a,b,c,d,e,f,g,h and i each represents 0 or 1 and the sum of $a+b+c$ is equal to the sum of $g+h+e$ and amounts to 0, 1 or 2; and when $a+b+c=1$ or 2, then the sum of $d+e+f$ is less than this by 1, i.e. $d+e+f=0$ or 1, and when $a+b+c=0$, its value is also 0; $n=0$, 1, 2 or 3, preferably 0;

A represents a monovalent, divalent or trivalent, (and preferably monovalent or divalent), optionally $C_1$-$C_4$-alkyl-substituted aromatic hydrocarbon group which preferably corresponds to the aromatic hydrocarbon group of the aromatic nitro compound used in the process according to the invention and R represents an aliphatic, cycloaliphatic or araliphatic hydrocarbon group generally having up to 18 carbon atoms and preferably corresponds to the hydrocarbon group of the alcohol component used in the process of the invention.

The following are examples of suitable catalyst components (d): aniline; o-, m- and p-toluidine; the isomeric nitroanilines; the isomeric diaminobenzenes; N,N'-diphenylurea; N,N-bis-(2-methyl-5-nitro-phenyl)-urea; N,N'-bis-(2-methyl-5-ethoxy-carbonylamino-phenyl)-urea; N,N'-bis-(2-methyl-5-aminophenyl)-urea; 2-amino-4-nitrotoluene; 4-amino-2-nitrotoluene; 2-amino-4-ethoxycarbonylamino-toluene; 4-amino-2-ethoxycarbonylamino-toluene; 2,4-diaminotoluene; N,N'-bis-(3-nitro-4-methylphenyl)-urea; N,N'-bis-(2-methyl-5-nitrophenyl)-urea; N,N'-bis-(3-ethoxycarbonylamino-4-methylphenyl)-urea; N,N'-bis-(2-methyl-5-ethoxycarbonylaminophenyl)-urea; N,N'-bis-(3-amino-4-methylphenyl)-urea; N,N'-bis-(2-methyl-5-aminophenyl)-urea; N-(3-nitro-4-methyl-phenyl)-N'-(2-methyl-5-nitrophenyl)- urea; N-(3-ethoxycarbonylamino-4-methylphenyl)-N'-(2-methyl-5-ethoxycarbonylamino-phenyl)-urea; N-(3-amino-4-methylphenyl)-N'-(2-methyl-5-aminophenyl)-urea; N-(3-nitro-4-methylphenyl)-N'-(3-ethoxycarbonylamino-4-methylphenyl)-urea; N-(3-nitro-4-methylphenyl)-N'-(2-methyl-5-ethoxycarbonylaminophenyl)- urea; N-(3-nitro-4-methylphenyl)-N'-(3-amino-4-methylphenyl)- urea; N-(3-nitro-4-methylphenyl)-N'-(2-methyl-5-aminophenyl)- urea; N-(2-methyl-5-nitrophenyl)-N'-(3-ethoxycarbonylamino-4-methylphenyl)-urea; N-(2-methyl-5-nitrophenyl)-N'-(2-methyl-5-ethoxycarbonylaminophenyl)-urea; N-(2-methyl-5-nitrophenyl)-N'-(3-amino-4-methylphenyl)- urea; N-(2-methyl-5-nitrophenyl)-N'-(2methyl-5-aminophenyl)-urea; N-(3-ethoxycarbonylamino-4-methylphenyl)-N'-(2-methyl-5-aminophenyl)-urea; N-(2-methyl-5-ethoxycarbonylaminophenyl)-N'-(3-amino-4-methylphenyl)- urea; N-(2methyl-5-ethoxycarbonylaminophenyl)-N'-(2-methyl-5-aminophenyl)-urea, and any mixtures of the compounds mentioned above as examples. As already mentioned above, it is preferred to use compounds (d) which correspond in their aromatic portion to the aromatic nitro compound used in the process according to the invention. Thus, for example, aniline or diphenylurea are used for nitrobenzene whereas a tolylamine or a ditolyl urea is used with nitrotoluene. By the same token, when divalent nitro compounds such as 2,4-dinitrotoluene are used, the corresponding compounds containing disubstituted tolyl groups are preferably used.

Higher homologues of the ureas exemplified above, i.e. compounds containing several urea units, may also be used.

When carrying out the process according to the invention, the reactants are generally used in such quantities that from 1 to 50, preferably from 5 to 30 hydroxyl groups of the alcohol component are present for each nitro group of the aromatic compound used as starting material. Carbon monoxide is generally used in excess over aromatic nitro compounds since the process is always carried out in a carbon monoxide atmosphere, which may also contain the oxygen used for the process according to the invention.

Catalyst component (a), i.e. elementary selenium or the selenium compound, which may be applied to a suitable carrier such as carbon, aluminum oxide, silicon dioxide, diactomaceous earth, activated clay, zeolite, molecular sieves, barium sulphate, calcium carbonate, ion exchange resins or similar materials, is used in a quantity which corresponds to 0.1 to 10% by weight, preferably 0.1 to 3% by weight of selenium, based on the quantity of nitro compound used as starting material.

When the oxidizing agent used as catalyst component (b) is oxygen or an oxygen containing gas, the oxygen should amount to from 0.01 to 6.0 volume %, preferably 0.1 to 2 volume %, based on the quantity of carbon monoxide. For safety reasons, it should not exceed 6.0 volume %. If oxidizing metal compounds are used as component (b), their quantity is generally from 0.1 to 100% by weight, preferably 5 to 40% by weight, based on the quantity of nitro compound.

The quantity of catalyst component (c) in the reaction mixture is generally from 1 to 40 mol %, and preferably from 4 to 25 mol %, based on the nitro compound used as starting material, these figures applying to the total quantity of basic compounds but not to the salts of formula MeX which may be added.

The quantity of catalyst component (d) in the reaction mixture is generally from 1 to 40 mol %, and preferably from 4 to 25 mol %, based on the nitro compound used as starting material.

The process according to the invention may be carried out in the absence of solvent since the alcohol itself serves as solvent, although a solvent may also be used. Examples of suitable solvents include aromatic solvents such as benzene, toluene, xylene, etc., nitriles such as acetonitrile, benzonitrile, etc., sulphones such as Sulfolan, aliphatic halogenated hydrocarbons such as 1,1,2-trichloro-1,2,2-trifluoroethane, aromatic halogenated hydrocarbons such as monochlorobenzene, dichlorobenzene, trichlorobenzene, and the like, ketones, esters and other solvents such as tetrahydrofuran, 1,4-dioxane, 1,2-dimethoxyethane and the like.

There is no restriction on the order in which the starting materials and catalyst system are added and the sequence may be varied as desired according to the nature of the apparatus used. For example, a starting mixture of alcohol, selenium catalyst, oxidizing agent, organic base, amine and/or urea compound and organic nitro compound may be introduced into a suitable pressure resistant reactor such as an autoclave, whereupon carbon monoxide may be introduced under pressure. The mixture may then be heated and stirred until the formation of urethane is completed. Carbon monoxide and optionally also the oxidizing agent may be introduced continuously or semicontinuously into the reactor while the carbon dioxide continuously formed during the reaction is removed. The reaction may be carried out batchwise, semicontinuously or continuously. The carbon monoxide present in excess after termination of the reacton may be renewed by recycling.

The reaction temperature is generally maintained within the range of from 80° to 220° C., preferably from 120° to 200° C. Although the reaction proceeds more rapidly at higher temperatures, there is a tendency to thermal decomposition at temperatures above 220° C., so that the yield of urethane product is reduced. The reaction pressure, i.e. the initial carbon monoxide pressure before the reaction mixture begins to be heated, is generally within the range of from 10 to 300 bar, and preferably from 20 to 150 bar. The reaction time depends upon the nature of the nitro compound used, the reaction temperature, the reaction pressure, the nature and quantity of catalyst and the nature of the apparatus but is generally within the range of from 5 minutes to 6 hours. After termination of the reaction which is indicated by a constant pressure (no further CO-consumption), the reaction mixture is either left to cool or is actively cooled. After the gas introduced into the reaction vessel has been discharged, the reaction mixture is filtered, distilled or separated by some other suitable method to isolate the urethane formed.

The reaction components left behind after removal of the urethane contain the catalyst system and any residues of urethane which have not been separated. It is advantageous to recover these residues, particularly if the process is carried out continuously.

Care should be taken to exclude water when carrying out the process according to the invention because partial hydrolytic decomposition of the products obtained by the process of the invention cannot be completely prevented in the presence of water in spite of the addition of catalyst component (d).

The essential feature of the invention when carrying out the process according to the invention resides in the use of an oxidizing agent which, used in combination with the catalyst system according to the invention, allows an excellent catalytic activity to be obtained even if the quantity of selenium in the catalyst system is substantially reduced. At the moment, there is no plausible explanation for the unexpected effect of these compounds.

The products of the process according to the invention are valuable intermediate products for the production of pesticides and polyurethanes. The products according to the invention are particularly suitable as starting materials for the preparation of the corresponding isocyanates or polyisocyanates by the known reaction of decomposition of the alcohol component.

The examples given below serve to illustrate the invention without restricting it. All of the reactions in the examples were carried out in a stainless steel (V 4 A) autoclave equipped with a stirrer. The yields given in the examples were calculated in each case from the results of gas chromatography and liquid chromatography.

EXAMPLES

EXAMPLE 1

17.22 g of nitrobenzene, 2.45 g of diazabicyclo [2,2,2]-octane, 1.94 g of potassium thiocyanate, 0.14 g of metallic selenium, 2.66 of aniline and 140 g of dry ethanol were introduced into a 0.7 l autoclave. The autoclave was washed out with dry air for 5 minutes and carbon monoxide was then introduced into the autoclave under pressure until the initial pressure was 100 bar at room temperature. The reaction system was heated to 160° C. with stirring and then stirred for a further one hour at 160° C. It was then left to cool to room temperature, the pressure was released, the reaction vessel was flushed with nitrogen and solid selenium was separated by filtration. The filtrate obtained was subjected to gas chromatographic analysis which showed that 90% of the nitrobenzene had been converted and the filtrate contained 21.7 g of ethyl-N-phenylcarbamate. 0.4 g of the aniline originally introduced remained in the reaction solution. Gas analysis showed that the gas space of the reaction system contained 0.8 volume % of oxygen at the beginning of the reaction and 0.3 volume % of oxygen after the reaction.

COMPARISON EXAMPLE 1a

Example 1 was repeated without flushing with air but the reaction system was flushed with nitrogen before the beginning of the reaction and subsequently with carbon monoxide. After the introduction of carbon monoxide under a pressure of 100 bar, the procedure was the same as in Example 1. Only 33.7% of the nitrobenzene was converted. The filtrate contained 10.2 g of ethyl-N-phenylcarbamate and 0.5 g of aniline.

COMPARISON EXAMPLE 1b

Example 1 was repeated without potassium thiocyanate. Only 12.8% of the nitrobenzene was converted. The filtrate contained 3.0 g of ethyl-N-phenylcarbamate and 1.47 g of aniline.

COMPARISON EXAMPLE 1c

Example 1 was repeated without aniline. Only 10.5% of the nitrobenzene was converted. The filtrate contained 1.4 g of ethyl-N-phenylcarbamate.

EXAMPLE 2

17.22 g of nitrobenzene, 2.45 g of diazabicyclo-[2,2,2]-octane, 0.7 g of metallic selenium, 2.66 g of aniline, 5 g of iron-III oxide and 140 g of dry ethanol were introduced into a 0.7 liter autoclave. The autoclave was flushed with nitrogen and then with carbon monoxide. Carbon monoxide was subsequently introduced into the autoclave under pressure until the starting pressure was 50 bar. The reaction mixture was heated to 160° C. with stirring, and stirring was then continued for 30 minutes at 160° C. Gas chromatographic analysis indicated quantitative conversion of the nitrobenzene and of the aniline added. The filtrate contained 25.3 g of ethyl-N-phenyl carbamate.

COMPARISON EXAMPLE

Example 2 was repeated without the addition of iron-III oxide. 55.5% of the nitrobenzene was converted. The filtrate contained 13.8 g of ethyl-N-phenylcarbamate and 0.3 g of aniline.

EXAMPLE 3

17.22 g of nitrobenzene, 1.05 g of 1,8-diazabicyclo [5,4,0]-undecene-7, 0.14 g of metallic selenium, 2.66 g of aniline and 140 g of dry ethanol were flushed with dry air as in Example 1 and reacted. The nitrobenzene was quantitatively converted and the filtrate contained 23.3 g of ethyl-N-phenylcarbamate. 0.35 g of the aniline introduced remained in the reaction solution.

COMPARISON EXAMPLE

Example 3 was repeated without flushing the reaction system with air but the system was flushed with nitrogen before the beginning of the reaction and then with carbon monoxide. 79.7% of the nitrobenzene was converted. The filtrate contained 18.3 g of ethyl-N-phenylcarbamate and 0.53 g of aniline.

EXAMPLE 4

17.22 g of nitrobenzene, 1.05 g of 1,8-diazabicyclo [5,4,0] undecene-7, 0.14 g of metallic selenium, 2.60 g of aniline, 140 g of dry ethanol and 2.5 g of 1,4-benzoquinone were introduced into a 0.7 liter autoclave. The autoclave was flushed with nitrogen and then with carbon monoxide. Carbon monoxide was then introduced into the autoclave under pressure until the starting pressure reached 100 bar. The reaction mixture was heated to 160° C. with stirring which was then continued for one hour at 160° C. 91.2% of the nitrobenzene was converted. The filtrate contained 22.8 g of ethyl-N-phenylcarbamate and 0.58 g of aniline.

EXAMPLE 5

17.22 g of nitrobenzene, 2.45 g of diazabicyclo[2,2,2]-octane, 1.62 g of potassium cyanate, 0.14 g of metallic selenium, 2.66 g of aniline, 140 g of dry ethanol and 2.5 g of a metal oxide mixture of iron-III oxide and vanadium pentoxide in proportions by weight of 11:1 were reacted as in Example 4. 98.9% of the nitrobenzene was converted and the filtrate contained 25.0 g of ethyl-N-phenylcarbamate and 0.24 g of aniline.

COMPARISON EXAMPLE

Example 5 was repeated without the addition of the metal oxide mixture. 16.4% of the nitrobenzene was converted. 6.2 g of ethyl-N-phenylcarbamate were detected in the filtrate.

EXAMPLE 6

Example 5 was repeated with 2.5 g of 1,4-benzoquinone instead of the metal oxide mixture. 78% of the nitrobenzene was converted. The filtrate could be shown to contain 20.1 g of ethyl-N-phenylcarbamate.

EXAMPLE 7

17.22 g of nitrobenzene, 2.45 g of diazabicyclo[2,2,2]-octane, 1.96 g of potassium acetate, 0.14 g of metallic selenium, 2.66 g of aniline, 140 g of dry ethanol and 2.5 g of the metal oxide mixture according to Example 5, were reacted as described in Example 4. Nitrobenzene was converted quantitatively. The filtrate contained 26.2 g of ethyl-N-phenylcarbamate and 0.2 g of aniline.

COMPARISON EXAMPLE

Example 7 was repeated without the addition of the metal oxide mixture. 50.5% of the nitrobenzene was converted and the filtrate contained 15.0 g of ethyl-N-phenylcarbamate.

EXAMPLE 8

17.22 g of nitrobenzene, 1.96 g of potassium acetate, 0.14 g of metallic selenium, 2.66 g of aniline, 140 g of dry ethanol and 2.5 g of the metal oxide mixture according to Example 5 were reacted as in Example 4. Nitrobenzene was converted quantitatively. The filtrate contained 24.7 g of ethyl-N-phenylcarbamate and 0.52 g of aniline.

COMPARISON EXAMPLE

Example 8 was repeated without the addition of the metal oxide mixture. 35.3% of the nitrobenzene was converted. 11.0 g of ethyl-N-phenylcarbamate were detected in the filtrate.

EXAMPLE 9

Example 8 was repeated using 6 g of N,N'-diphenylurea instead of aniline. Nitrobenzene was converted quantitatively and the filtrate contained 24.5 g of ethyl-N-phenylcarbamate.

EXAMPLE 10

Example 8 was repeated but the proportion by weight of iron-III oxide to vanadium pentoxide was changed to 10:1. Nitrobenzene was converted quantitatively. The filtrate contained 23.2 g of ethyl-N-phenylcarbamate and 1.8 g of aniline.

EXAMPLE 11

25.46 g of 2,4-dinitrotoluene, 3.32 g of 1,8-diazabicyclo[5,4,0]-undecene-7, 0.5 g of metallic selenium, 3.5 g of 2,4-diaminotoluene and 140 g of dry ethanol were introduced into a 0.7 liter autoclave. The autoclave was flushed with dry air for 5 minutes and carbon monoxide was then introduced under pressure until a starting pressure of 100 bar was reached. The reaction mixture was maintained at 170° C. for one hour with stirring. After removal of selenium by filtration liquid chromatography analysis showed that 2,4-dinitrotoluene had been converted quantitatively. The filtrate contained 24.7 g of 2,4-diethoxycarbonylaminotoluene, 4.8 g of 2-nitro-4-ethoxycarbonylamino-toluene and 0.8 g of 4-nitro-2-ethoxycarbonylamino-toluene.

COMPARISON EXAMPLE

Example 11 was repeated without flushing with air but the reaction mixture was flushed with nitrogen before the beginning of the reaction and then with carbon monoxide. Carbon monoxide was forced in up to a pressure of 100 bar and the process was then carried out as in Example 11. The filtrate contained 10.0 g of 2,4-diethoxycarbonylaminotoluene, 9.9 g of 2-nitro-4-ethoxycarbonylamino-toluene and 7.7 g of 4-nitro-2-ethoxycarbonylamino-toluene.

EXAMPLE 12

25.46 g of 2,4-dinitrotoluene, 1.96 g of potassium acetate, 0.5 g of metallic selenium, 3.5 g of 2,4-diaminotoluene, 140 g of dry ethanol and 2.5 g of the metal oxide mixture according to Example 5 were introduced into a 0.7 liter autoclave. The air in the autoclave was replaced by nitrogen and then by carbon monoxide. Carbon monoxide was then introduced into the autoclave under pressure until the starting pressure of 100 bar was reached at room temperature. The reaction system was heated with stirring and maintained at 170° C. for one hour. When the filtrate was analyzed by liquid chromatography, it was found that 2,4-dinitrotoluene had been converted quantitatively. The filtrate contained 28.6 g of 2,4-diethoxy-carbonylaminotoluene.

COMPARISON EXAMPLE

Example 12 was repeated without the addition of metal oxide mixture. The filtrate contained 19.2 g of 2,4-diethoxycarbonylaminotoluene, 6.0 g of 2-nitro-4-ethoxycarbonylaminotoluene and 5.5 g of 4-nitro-2-ethoxycarbonylaminotoluene.

EXAMPLE 13

25.34 g of 2,4-dinitrotoluene, 0.7 g of potassium acetate, 0.5 g of metallic selenium, 2.8 g of 2-amino-4-nitrotoluene, 1.4 g of 4-amino-2-nitrotoluene, 140 g of dry ethanol and 2.5 g of the metal oxide mixture according to Example 5 were heated to 170° C. for 40 minutes.

2,4-Dinitrotoluene was converted quantitatively. The filtrate contained 23.8 g of 2,4-diethoxycarbonylaminotoluene.

COMPARISON EXAMPLE

Example 13 was repeated without the addition of metal oxide mixture. Quantitative analysis (thin layer chromatography: silica gel 60 F 254 of Merck, ether/ligroin 1:1 as eluant) showed that 2,4-dinitrotoluene and the isomeric nitro-ethoxycarbonylamino-toluenes were present as main products of the reaction mixture. 2,4-Diethoxycarbonylamino-toluene could only be detected in traces. Quantitative analysis was not carried out because the nitro compound used as starting material causes separation problems in liquid chromatography.

EXAMPLE 14

25.46 g of 2,4-dinitrotoluene, 1.96 g of potassium acetate, 0.28 g of metallic selenium, 3.5 g of 2,4-diaminotoluene, 140 g of dry ethanol and 2.5 g of a metal oxide mixture of iron-III oxide and vanadium pentoxide in proportions by weight of 1:1 were reacted as described in Example 12. The filtrate contained 28.2 g of 2,4-diethoxycarbonylamino-toluene.

EXAMPLE 15

Example 14 was repeated but with the ratio by weight of iron-III oxide to vanadium pentoxide changed to 11:1. The filtrate contained 32.5 g of 2,4-diethoxycarbonylamino-toluene.

COMPARISON EXAMPLE

Example 15 was repeated without the addition of metal oxide mixture. The filtrate contained 10.0 g of 2,4-diethoxycarbonylamino-toluene, 7.8 g of 2-nitro-4-ethoxycarbonylamino-toluene and 10.5 g of 4-nitro-2-ethoxycarbonylamino-toluene.

What is claimed is:

1. A process for the preparation of urethanes by the reaction of aromatic nitro compounds with aliphatic, cycloaliphatic or araliphatic alcohols and carbon monoxide in the presence of catalyst systems containing selenium and/or selenium compounds and aromatic amino compounds and/or aromatic urea compound, characterized in that the catalyst systems used contain (a) tertiary organic amines and/or alkali metal salts of weak acids and (b) oxidizing agents selected from the group consisting of oxygen, oxidizing organic compounds containing chemically bound oxygen and oxidizing inorganic compounds of metals of sub-Groups 1,2 and 5–8 of the Periodic System of Elements containing chemically bound oxygen.

2. The process of claim 1, characterized in that the tertiary amine used is diazabicyclo[2,2,2]-octane.

3. The process of claim 1, characterized in that the tertiary amine is used in combination with a salt corresponding to the formula MeX in which
Me represents an alkali metal cation and
X represents an iodide, cyanate or thiocyanate anion.

4. The process of claim 1, characterized in that the aromatic nitro compound used is nitrobenzene.

5. The process of claim 3, characterized in that the aromatic nitro compound used is dinitrotoluene.

6. The process of claims 1 or 5, characterized in that the alcohol used is ethyl alcohol.

7. A process for the preparation of urethanes comprising reacting an aromatic nitro compound with an aliphatic, cycloaliphatic or araliphatic alcohol and carbon monoxide in the presence of
   (a) selenium and/or a selenium compound;
   (b) an oxidizing agent;
   (c) a tertiary organic amine and/or an alkali metal salt of a weak acid; and
   (d) an aromatic amine compound and/or an aromatic urea compound.

8. The process of claim 7, wherein a mixture of tertiary organic amine and alkali metal salt of a weak acid is used as component (c), said salt being used in an amount of from 1 to b 40 mol percent based on the quantity of nitro compound present.

9. The process of claim 8, wherein said salt is used in an amount of from 4 to 20 mol percent based on the quantity of nitro compound present.

10. The process of claim 7, wherein the amounts of reactants are such that 1 to 50 hydroxyl groups of the alcohol are present for each nitro group.

11. The process of claim 7, wherein the amount of component (a) is from 0.1 to 10 percent by weight based on the quantity of nitro compound used.

12. The process of claim 7, wherein component (b) is oxygen or an oxygen containing gas and amounts to from 0.01 to 6 volume percent based on the amount of carbon monoxide.

13. The process of claim 7, wherein component (b) is an oxidizing metal compound and is used in an amount of from 0.1 to 100 percent by weight based on the amount of nitro compound.

14. The process of claim 7, wherein component (c) is used in an amount of from 1 to 40 mol percent based on the nitro compound.

15. The process of claim 7, wherein component (d) is used in an amount of from 1 to 40 mol percent based on the nitro compound.

16. The process of claim 7, wherein the reaction temperature is maintained at from 80° to 220° C.

17. The process of claim 16, wherein the reaction pressure is from 10 to 300 bar, and the reaction time is from 5 to 6 hours.

* * * * *